United States Patent

Lacombe

[11] Patent Number: 5,354,332
[45] Date of Patent: Oct. 11, 1994

[54] ATIFICIAL CORNEA

[76] Inventor: Emmanuel Lacombe, 78, Avenue de la Grande Armée, 75017 Paris, France

[21] Appl. No.: 23,873

[22] Filed: Feb. 26, 1993

Related U.S. Application Data

[63] Continuation of Ser. No. 739,901, Aug. 2, 1991, abandoned.

[30] Foreign Application Priority Data

Aug. 2, 1990 [FR] France .................. 90 09915

[51] Int. Cl.$^5$ .............................................. A61F 2/14
[52] U.S. Cl. ................................................. 623/5
[58] Field of Search ........................... 623/4, 5

[56] References Cited

U.S. PATENT DOCUMENTS

| 2,754,520 | 7/1956 | Crawford, Jr. | 623/5 |
| 4,470,159 | 9/1984 | Peyman | 623/5 |
| 4,923,466 | 5/1990 | Pintucci | 623/5 |

FOREIGN PATENT DOCUMENTS

| 562277 | 8/1977 | U.S.S.R. | 623/5 |
| 1044420 | 5/1965 | United Kingdom | 623/5 |

OTHER PUBLICATIONS

Louis Girard, *Advanced Techniques in Ophthalmic Microsurgery vol. II Corneal Surgery*, C. V. Mosby Co., 1981, pp. 243–260.

*Acrylic Corneal Implant in Keratoplasty*, Gyorffy, Amer. Journal of Ophthalmology, vol. 34, #5, part. 1, May 1951, p. 757.

*Primary Examiner*—Randy C. Shay
*Attorney, Agent, or Firm*—Ziesenheim Bruening Logsdon Orkin & Hanson Webb

[57] ABSTRACT

The invention relates to an artificial cornea comprising a transparent optical part placed in an orifice formed in the cornea. Its posterior end is fixed to a support part by being screwed thereto. The support part is pressed against the inside wall of the cornea. To assist in holding the support part, the prosthesis may include a fixing part which exerts forwards traction on the optical part and thus on the support part.

18 Claims, 2 Drawing Sheets

ATIFICIAL CORNEA

This is a continuation of copending application Ser. No. 07/739,901 filed on Aug. 2, 1991 abandoned.

The present invention relates to an artificial cornea.

More precisely, the invention relates to an optical prosthesis which may be installed by performing a central trephination in the cornea when the cornea can no longer fulfill its function of being transparent.

BACKGROUND OF THE INVENTION

Certain kinds of blindness can be caused by the optical properties of the cornea being spoilt or rendered opaque. In some cases, this can be remedied by keratoplasty, i.e. by replacing the diseased portion of the cornea by a fragment of healthy and transparent cornea from a donor. However, if lesions from which the cornea is suffering are too great (burns, dry syndrome, pemphigoid, . . . ), it is necessary to make use of palliative surgery which consists in making an orifice or trephination in the diseased portion of the cornea and in installing a prosthesis constituting an artificial cornea, with this technique being called "keratoprosthesis".

Two keratoprosthesis techniques are already well known: Strampelli's odonto-keratoprosthesis; and Choyce's keratoprosthesis technique. These surgical techniques provide the prosthesis support either with an anterior fixing on the cornea, or else with an intra-corneal fixing.

These techniques suffer from various drawbacks.

Firstly the surgery is major and can give rise to serious post-operative complications that often lead to results that are disappointing for the patient from beth the anatomical and the functional points of view. The above-recalled techniques for fixing the prosthesis run the risk of the patient suffering necrosis where there is overlap between the prosthesis and tissue, and this may lead to the prosthesis being expelled.

Secondly, when prostheses of the types mentioned above are installed, it is often observed that a fibrous film forms over the posterior face of the cornea and also over the posterior face of the prosthesis, thus giving rise to an unsuccessful operation insofar as the prosthesis becomes at least partially inoperative.

An object of the invention is to provide a prosthesis constituting an artificial cornea that remedies the above-outlined drawbacks.

SUMMARY OF THE INVENTION

According to the invention, this object is achieved by an artificial cornea that comprises:

an optical part which is transparent, at least in part, which is generally in the form of a cylinder whose right cross-section is substantially identical to that of the orifice formed in the cornea, which has a first end, and which has a second end that is situated inside the anterior chamber of the eye when said optical part has been put into place;

a support part fixed at least to the second end of said optical part, surrounding said second end, and having a bearing face facing the posterior face of the cornea when said support part has been put into place, the outside dimensions of said support part being greater than the outside dimensions of the right cross-section of said orifice; and fixing means for at least temporarily pressing said bearing face of said support part against the posterior face of the cornea at the periphery of said orifice.

It will thus be understood that final fixing of the prosthesis in the cornea is obtained in particular by the posterior wall of the cornea adhering to the support part, thus also making it possible to obtain a sealed connection between the prosthesis and the cornea, thereby making it possible to avoid the keratoprosthesis being expelled. Preferably, said support part further includes means for at least temporarily positioning and fixing said support part on the posterior face of the cornea.

Also preferably, said fixing means comprise a fixing part outside the eye, fixed to the first end of the optical part, and having its periphery bearing against the periphery of the front face of the cornea.

In a preferred embodiment, said optical part is fixed to said support part by a co-operating screw thread and tapping formed at the second end of the optical part and in the support part.

BRIEF DESCRIPTION OF THE DRAWINGS

An embodiment of the invention is described by way of example with reference to the accompanying drawings, in which.

DETAILED DESCRIPTION

Figure 1:
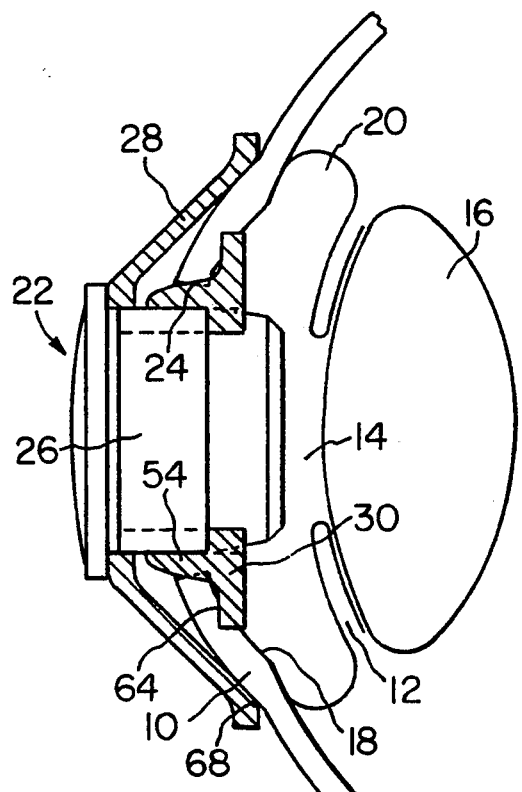
FIG. 1 is a fragmentary vertical section view through an eyeball in which a keratoprosthesis of the invention has been installed.
Figure 2:
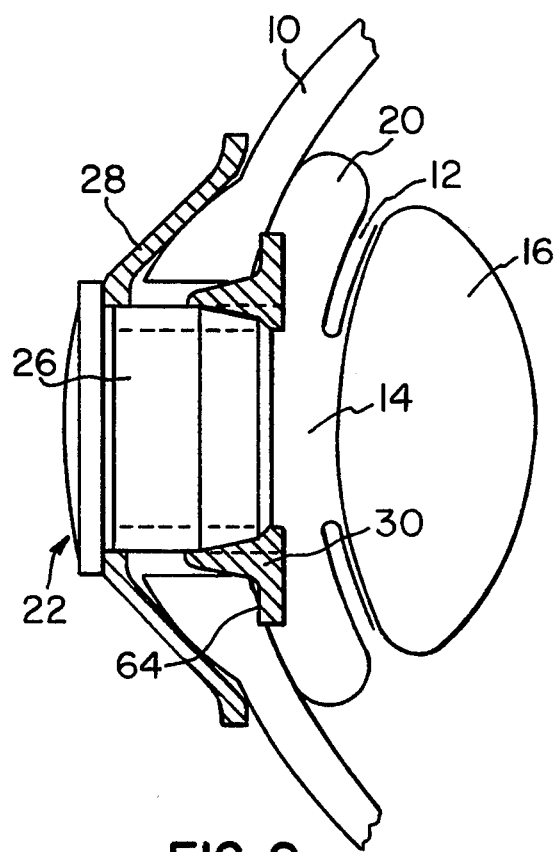
FIG. 2 is analogous to FIG. 1 but shows a cornea of greater central thickness.

With reference initially to FIG. 1, the general organization of the keratoprosthesis and the way in which it is installed in the eye are described.

FIG. 1 is a vertical section through the anterior portion of an eyeball. In particular, there can be seen the cornea 10, the iris 12 with its pupil 14, and the lens 16 which is naturally situated behind the iris 12 and the pupil 14. Between the iris 12 and the posterior face 18 of the cornea 10 there is the anterior chamber 20 of the eye. As mentioned above, the artificial cornea given overall reference 22 is placed in an orifice or trephination 24 which is formed in the cornea 10. As shown in simplified manner in FIG. 1, the prosthesis 22 essentially comprises three parts. Firstly there is an optical part 26 made of transparent material and having the function of replacing the diseased part of the cornea 10. The prosthesis includes a support part 80 whose periphery bears against the posterior wall 18 of the cornea 10. The support part 30 is fixed to the posterior end of the optical part 26. Finally, the prosthesis may include a fixing part 28 which is disposed on the outside of the cornea and which is fixed to the front end of the optical part 26 while also bearing against the periphery of the anterior portion 10 of the cornea.

The preferred embodiment of the three parts constituting the implant 22 are now described with reference to FIG. 8.

The optical part 26 is made of a transparent material. For example the part 26 may be made of polymethylmethacrylate (PMMA), better known under the trademark Plexiglas. The general shape of the part 26 is that of a right circular cylinder 32 about an axis X—X'. The cylinder 32 has a first end 34 or "anterior" end, and a second end 36 or "posterior" end. The anterior end 34 is defined by a convex surface 38 which is designed to confer the desired optical parameters on the part 26. The end 34 also includes a flange 40 projecting radially outwards from the side face 42 of the cylinder 32. The second end 36 of the optical part 26 is plane. Finally, the side face 42 of the cylinder 32 is provided with a thread 44.

In the example shown, the optical part 26 has a total length L of about 4 millimeters, and its cylindrical portion 32 has a diameter D of about 5 millimeters. The dimensions of the optical part 26 and the curvature 38 of its front face are designed to produce an optical field of about 70° and for the optical system constituted in this way to have a vergency of about 40 diopters.

The fixing part 28 is generally in the form of a curved plate having two end bearing edges 48 that are flared at their ends. The center of the plate 46 is pierced by an axial orifice 50 whose diameter is large enough to allow the cylinder 32 of the optical path 26 to pass freely therethrough, but small enough to prevent the flange 40 from passing, thereby causing the flange to bear against the anterior face 52 of the central portion of the fixing part 28.

Figure 3:
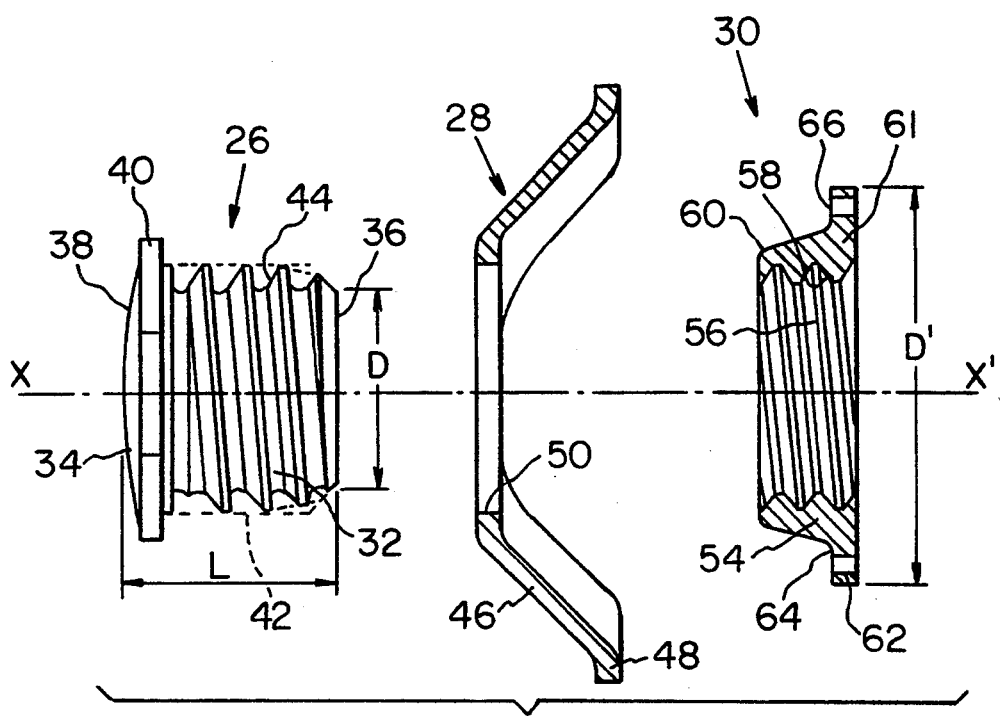
FIG. 3 is a vertical section view in three parts showing a preferred embodiment of a prosthesis of the invention.

The support part 30 can be seen to be generally in the form of a disk or a ring which is extended by a sleeve 54 whose axial orifice 56 is tapped at 58. The tapping 58 is designed to co-operate with the thread 54 on the side face of the optical part 26. It must be ensured that the optical part 26 is screwed into the support part 30 in a manner which is at least liquid-tight. As shown in FIG. 3, the side wall of the sleeve 54 is referenced 60 and is slightly conical. At its posterior end 61, the sleeve 54 is provided with a flange 62 which naturally projects outwards from the side wall 60. The anterior face 64 of the flange 62 constitutes a bearing face as explained below. In addition, it is preferable for the flange 64 to include orifices 66 uniformly distributed around its circumference. The diameter D' of the flange 62 is about 8 millimeters, i.e. significantly greater than the diameter of the orifice 24 provided through the cornea 10. It should also be added that the fixing part 28 and the support part 30 are preferably both made of PMMA.

Now that the preferred embodiment of the implant 10 has been described in detail, reference is made again to FIG. 1 while describing how the implant is installed in the cornea 10.

Figure 4:
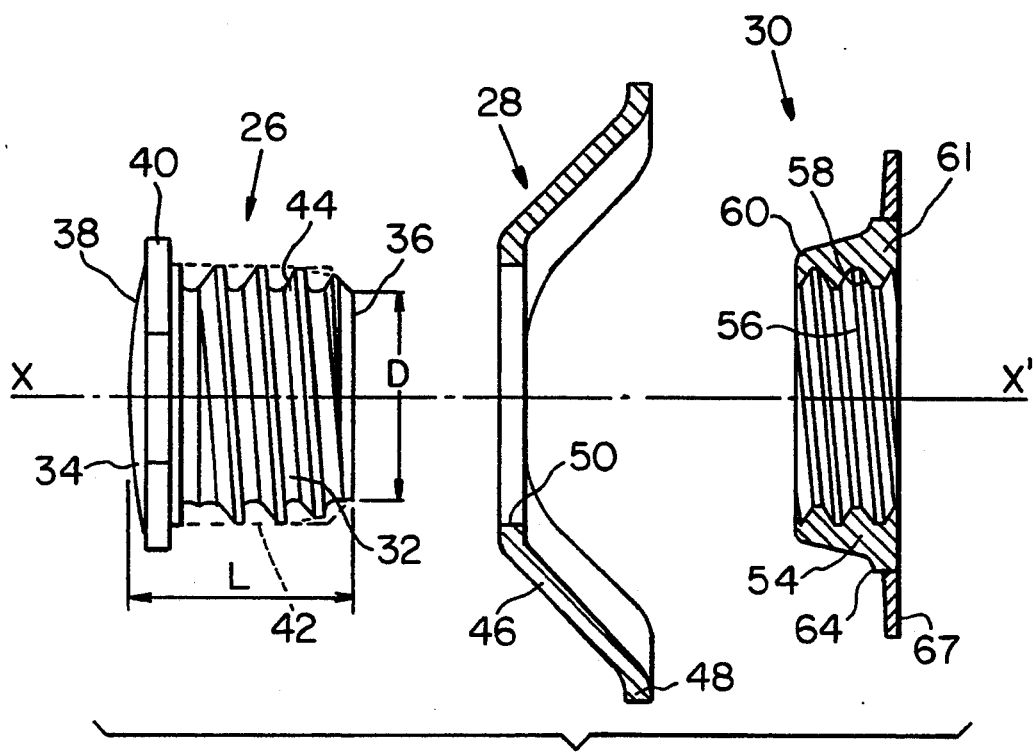
FIG. 4 is a vertical section view in three parts showing a second embodiment of the prosthesis of the present invention.

Initially, and in conventional manner, the trephination 24 is formed in the center of the cornea. Thereafter, the support part 30 is put into place in the anterior chamber 20 by using the techniques that are conventionally used for anterior chamber prosthesis, and this is done in such a manner that the bearing face 64 of the flange 62 is placed against the posterior face 18 of the cornea, while the sleeve 54 of this part is at least partially engaged in the orifice 24 of the cornea. For example, the support part 30 is inserted in the anterior chamber by an incision formed at the periphery of the cornea. Once installed in this way, the part 30 is positioned and fixed by means of a suture through the cornea using the orifices 66 formed in the part 30. In a variant, the support part 30, as shown in FIG. 4, may be surrounded by porous fabric 67 suitable for colonization, and the transcorneal suture is then performed in the fabric.

In a later step, the fixing part 28 is placed around the cylinder 32 of the optical part 26 in such a manner that the anterior face 52 of the part 28 is in contact against the flange 40 of the optical part 26. The posterior end 36 of the optical part 26 is then engaged in the orifice 24 in the cornea so that the optical part penetrates into the tapped orifice 56 in the support part 30. The part 26 is then screwed into the support part 30. While screwing is taking place, the periphery 48 of the fixing part 28 which has a degree of resilience comes to bear against the sclera 68 or against the periphery of the cornea 10, as shown in FIG. 1. Screwing is stopped when firstly the optical part 26 is properly positioned relative to the cornea and relative to the anterior chamber 20, and secondly the fixing part 28 which is partially resilient exerts a suitable traction force on the optical part 26. Given the resilience of the part 30, the bearing face 64 of the part 30 is pressed firmly against the posterior wall 18 of the cornea. In addition, the pressure exerted by the aqueous humor on the posterior faces of the parts 26 and 30 enhances this phenomenon. When the optical part 26 has been installed, it may be flush with the posterior face of the part 30 or it may project by about 1 millimeter beyond it. Because the optical part penetrates into the anterior chamber 20 in the projecting disposition, this disposition has the advantage of avoiding a film being formed on the posterior face of the optical part. Prosthesis installation is then terminated.

Adherence between the flange 64 of the support part 30 and the posterior wall 18 of the cornea is established progressively by adhesion. This adhesion also has the advantage of constituting a sealed connection between these two parts. The connection is further reinforced by the fact that a fibrous film usually forms on the posterior face of the support part Once scarring is fully completed and a final and sealed connection has thus been obtained between the part 30 and the posterior face of the cornea, it is possible to remove the fixing part 28. Thus the only parts of the prosthesis that remain are the support part 30 and the optical part 26. Naturally, it may be judged preferable in some cases to leave the fixing part 28 in place.

FIG. 3 shows another advantage of the invention. Because of the threaded connection between the support part 30 and the optical part 26, it is possible to fit the prosthesis to corneas of different central thicknesses merely by screwing the optical part 26 to a greater or lesser extent in the fixing part 30. In FIG. 1, the central thickness of the cornea is about 0.8 millimeters, whereas in FIG. 3 the same thickness is about 3 millimeters.

An additional advantage lies in the fact that in the embodiment described above, the optical part is screwed into the support part. It is therefore possible during the lifetime of the keratoprosthesis to change the optical part 26 to adapt to changes in the eyesight of the patient.

It is thus possible to consider using a keratoprosthesis as a support for a correcting optical system even if the cornea is healthy.

Figure 5:
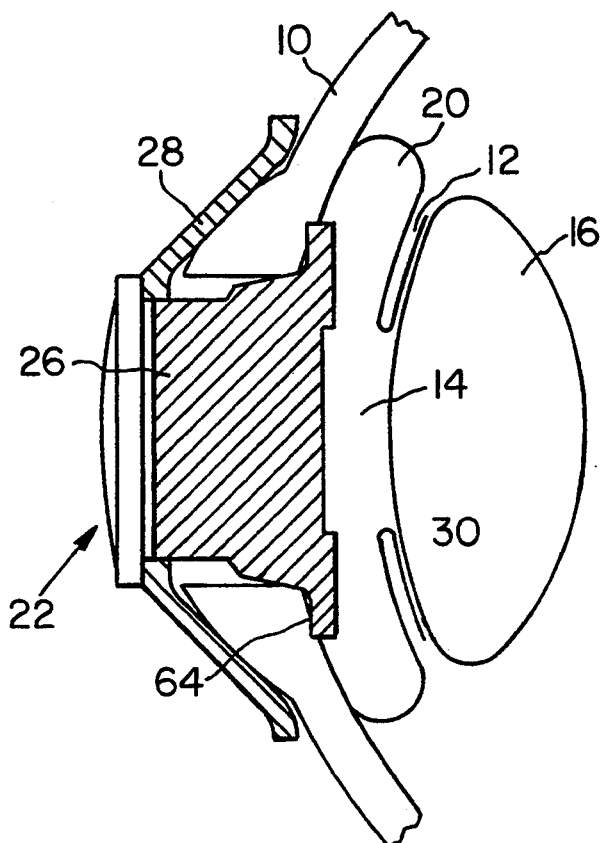
FIG. 5 is analogous to FIG. 1 and shows a third embodiment of the prosthesis of the present invention.

The above description relates to a preferred embodiment of the prosthesis of the invention. However, various other embodiments of the prosthesis may naturally be provided. In particular, the support part 30 and the optical part 26 may be made in the form of a single part which is placed as a whole in the cornea so as to obtain the configuration shown in FIG. 5. Similarly, the fixing part 28 may have some other shape. It merely requires means for fixing to the anterior end 34, 40 of the optical part 26 and second ends that bear against the periphery of the cornea to apply the required traction on the fixing part 30 via the optical part 26. In addition, it is desirable to give the fixing part 28 a suitable shape, e.g. flexible tabs integral with a ring, enabling it to be removed easily once the part 30 adheres suitably to the posterior face of the cornea.

In the preferred embodiment, the keratoprosthesis includes the fixing part 28. However, the invention covers a prosthesis that does not include this part. In some cases, the transcorneal suture of the support part plus the pressure exerted on the posterior face thereof by the aqueous humor filling the anterior chamber may suffice to urge the part 30 against the posterior face of the cornea.

I claim:

1. An artificial cornea consisting of:
   an optical part of which at least a portion is transparent, and which is generally in the form of a cylinder, said optical part having a first end and a second end, wherein said second end is situated inside the anterior chamber of the eye when said optical part has been put into place; and
   a support part made of a material adapted to have the posterior face of the cornea adhere thereto after said artificial cornea has been put into place, said support part at least fixed to said second end of said optical part, surrounding said second end, and having a bearing face facing the posterior face of the cornea when said support part has been put into place, the outside dimensions of said support part being greater than the outside dimensions of said cylinder, said support part having a posterior face turned towards the anterior chamber of the eye for receiving the pressure of the aqueous humor when said artificial cornea has been put into place, said support part being provided with orifices adapted to receive suture threads, wherein said support part is adapted to provide the sole support for said artificial cornea after said artificial cornea has been put into place and the posterior face of the cornea has adhered to said support part.

2. An artificial cornea according to claim 1, wherein said optical part is fixed to said support part by a co-operating screw thread and tapping formed at said second end of said optical part and in said support part.

3. An artificial cornea according to claim 1, wherein said optical part:
   is made entirely of transparent material;
   is generally in the form of a right circular cylinder;
   has a flange projecting outwards from said first end of said cylinder; and
   is threaded at least at said second end.

4. An artificial cornea according to claim 3, wherein said support part is generally in the form of a circular disk having two end faces and a central orifice, with said central orifice of said support part being tapped to co-operate with said thread of said optical part, and with the periphery of one of said end faces which is directed towards the posterior face of the cornea when said artificial cornea has been put into place, constituting said bearing face.

5. An artificial cornea according to claim 3, wherein the length of said cylinder constituting said optical part is about 4 millimeters and its diameter is about 5 millimeters.

6. An artificial cornea according to claim 1, wherein said optical part and said support part are constituted by a single part.

7. An artificial cornea according to claim 1, wherein said optical part and said support part are made of PMMA.

8. An artificial cornea according to claim 1, wherein said optical part has a vergency of about 40 diopters.

9. An artificial cornea consisting of:
   an optical part of which at least a portion is transparent, and which is generally in the form of a cylinder, said optical part having a first end and a second end, wherein said second end is situated inside the anterior chamber of the eye when said optical part has been put into place;
   a support part made of a material adapted to have the posterior face of the cornea adhere thereto after said artificial cornea has been put into place, said support part at least fixed to said second end of said optical part, surrounding said second end, and having a bearing face facing the posterior face of the cornea when said support part has been put into place, the outside dimensions of said support part being greater then the outside dimensions of said cylinder, said support part having a posterior face turned towards the anterior chamber of the eye for receiving the pressure of the aqueous humor when said artificial cornea has been put into place; and
   a colonizable porous fabric surrounding said support part and adapted to receive suture threads, wherein said support part and said colonizable porous fabric are adapted to provide the only support for said artificial cornea after said artificial cornea is positioned within the cornea and the posterior face of the cornea has adhered to said support part.

10. An artificial cornea according to claim 9, wherein said optical part is fixed to said support part by a co-operating screw thread and tapping formed at said second end of said optical part and in said support part.

11. An artificial cornea according to claim 9, wherein said optical part:
    is made entirely of transparent material;
    is generally in the form of a circular cylinder;
    has a flange projecting outwards from said first end of said cylinder; and
    is threaded at least at said second end.

12. An artificial cornea according to claim 11, wherein said support part is generally in the form of a circular disk having two end faces and a central orifice, with said central orifice of said support part being tapped to cooperate with said thread of said optical part, and with the periphery of one of said end faces which is directed towards the posterior face of the cornea when said artificial cornea has been put into place constituting said bearing face.

13. An artificial cornea according to claim 11, wherein the length of said cylinder constituting said optical part is about 4 millimeters and its diameter is about 5 millimeters.

14. An artificial cornea according to claim 9, wherein said optical part and said support part are constituted by a single part.

15. An artificial cornea according to claim 9, wherein said optical part and said support part are made of PMMA.

16. An artificial cornea according to claim 9, wherein said optical part has a vergency of about 40 diopters.

17. An artificial cornea kit consisting of:
   a plurality of interchangeable optical parts of which at least a portion of each said optical part is transparent, and each said optical part being generally in the form of a cylinder, each said optical part having a first end and a second end, wherein said second end is situated inside the anterior chamber of the eye when said optical part has been put into place; and
   a support part made of a material adapted to have the posterior face of the cornea adhere thereto when said artificial cornea has been put into place, said support part at least fixed to said second end of one of said optical parts, surrounding said second end, and having a bearing face facing the posterior face of the cornea when said support part has been put into place, the outside dimensions of said support part being greater than the outside dimensions of each said cylinder, said support part having a posterior face turned towards the anterior chamber of the eye for receiving the pressure of the aqueous humor when said artificial cornea has been put into place;
   wherein each of said optical parts has a different vision-correcting characteristic and wherein said support part is adapted to provide the sole support for said artificial cornea after said artificial cornea has been put into place and the posterior face of the cornea has adhered to said support part.

18. An artificial cornea according to claim 17, wherein said support part is provided with orifices adapted to receive suture threads.

* * * * *